US009517249B2

(12) United States Patent
Fast et al.

(10) Patent No.: US 9,517,249 B2
(45) Date of Patent: Dec. 13, 2016

(54) ANTIOXIDANT DIETARY SUPPLEMENT AND RELATED METHOD

(71) Applicant: Access Business Group International LLC, Ada, MI (US)

(72) Inventors: David J. Fast, Grand Rapids, MI (US); Jennifer Patterson, Grand Rapids, MI (US); Arun Rajgopal, Grand Rapids, MI (US); Donald J. Pusateri, Hemet, CA (US); Kevin W. Gellenbeck, Poway, CA (US); Jeffrey Scholten, Grand Rapids, MI (US); Steven R. Missler, Grand Rapids, MI (US); Russell K. Randolph, Anaheim, CA (US); Jennifer Chuang, Saratoga, CA (US); Yumei Lin, Long Beach, CA (US); Valiantsina Kazlova, Stanton, CA (US)

(73) Assignee: Access Business Group International LLC, Ada, MI (US)

( * ) Notice: Subject to any disclaimer, the term of this patent is extended or adjusted under 35 U.S.C. 154(b) by 169 days.

(21) Appl. No.: 14/088,765

(22) Filed: Nov. 25, 2013

(65) Prior Publication Data

US 2014/0147526 A1 May 29, 2014

Related U.S. Application Data

(60) Provisional application No. 61/729,919, filed on Nov. 26, 2012.

(51) Int. Cl.
| | | |
|---|---|---|
| *A61K 36/53* | (2006.01) | |
| *A61K 36/906* | (2006.01) | |
| *A61K 36/73* | (2006.01) | |
| *A61K 36/9066* | (2006.01) | |
| *A61K 36/31* | (2006.01) | |
| *A23L 1/30* | (2006.01) | |
| *A23L 2/52* | (2006.01) | |
| *A61K 31/352* | (2006.01) | |
| *A61K 45/06* | (2006.01) | |

(52) U.S. Cl.
CPC .......... *A61K 36/9066* (2013.01); *A23L 1/3002* (2013.01); *A23L 2/52* (2013.01); *A61K 31/352* (2013.01); *A61K 36/31* (2013.01); *A61K 36/53* (2013.01); *A61K 45/06* (2013.01)

(58) Field of Classification Search
CPC ...... A61K 36/60; A61K 36/82; A61K 36/906; A61K 36/53
USPC ................ 424/756, 747, 765, 777
See application file for complete search history.

(56) References Cited

U.S. PATENT DOCUMENTS

| | | | |
|---|---|---|---|
| 4,163,803 A | 8/1979 | Goldscher | |
| 5,077,069 A | 12/1991 | Chang et al. | |
| 5,804,168 A * | 9/1998 | Murad ............ | A61K 8/27 |
| | | | 424/400 |
| 5,897,865 A | 4/1999 | Nguyen | |
| 5,989,558 A | 11/1999 | Lopes | |
| 6,086,910 A | 7/2000 | Howard et al. | |
| 6,210,701 B1 | 4/2001 | Darland et al. | |
| 6,352,712 B1 * | 3/2002 | Lukaczer ............ | A23L 1/296 |
| | | | 424/439 |
| 6,387,416 B1 | 5/2002 | Newmark et al. | |
| 6,399,089 B1 | 6/2002 | Yegorova et al. | |
| 6,491,948 B1 | 12/2002 | Buchholz et al. | |
| 6,514,540 B1 | 2/2003 | Sobczak | |
| 6,534,086 B1 | 3/2003 | Krumhar | |
| 6,602,517 B2 | 8/2003 | Darland et al. | |
| 6,696,484 B2 | 2/2004 | Liao et al. | |
| 6,733,797 B1 | 5/2004 | Summers | |
| 6,827,945 B2 | 12/2004 | Rosenbloom | |
| 6,827,951 B2 | 12/2004 | Newmark et al. | |
| 6,949,260 B2 | 9/2005 | Krumhar | |
| 7,070,814 B2 | 7/2006 | Qazi et al. | |
| 7,128,933 B2 | 10/2006 | Kurk et al. | |

(Continued)

FOREIGN PATENT DOCUMENTS

| | | |
|---|---|---|
| CN | 101356974 A | 2/2009 |
| WO | 9213851 | 8/1992 |

(Continued)

OTHER PUBLICATIONS

Written Opinion, PCT/US2013/071597, Jun. 25, 2014.

(Continued)

*Primary Examiner* — Chris R Tate
*Assistant Examiner* — Deborah Davis
(74) *Attorney, Agent, or Firm* — Warner Norcross & Judd LLP

(57) ABSTRACT

A supplement including a blend of turmeric, quercetin and rosemary, or holy basil, wasabi, and broccoli seed extract which are present in a balanced and predetermined ratio, and which stimulate the Antioxidant Response Element (ARE), Quinone Reductase, and/or induce related gene expression, for example, heme oxygenase-1 (HMOX-1) expression. The blend of ingredients can be formed as or in a dietary supplement adapted for administration to a subject. The dietary supplement can be formulated so that the turmeric, quercetin and rosemary are present in a predetermined ratio of 1:3:5, or holy basil, wasabi, and broccoli seed extract in a predetermined ratio of 1:1:0.2. Additional ingredients can be included in the supplement. The supplement can synergistically affect natural antioxidant response pathways within cells of a subject to whom the supplement is administered. A related method of use is also provided.

10 Claims, 10 Drawing Sheets

(56) References Cited

U.S. PATENT DOCUMENTS

| | | |
|---|---|---|
| 7,241,461 B2 | 7/2007 | Myhill et al. |
| 7,429,397 B2 | 9/2008 | Palpu et al. |
| 7,682,636 B2 | 3/2010 | Babish et al. |
| 7,794,758 B2 | 9/2010 | Bartunek et al. |
| 7,883,728 B2 | 2/2011 | Antony |
| 8,044,096 B2 | 10/2011 | Lines |
| 8,420,132 B2 | 4/2013 | Gokaraju et al. |
| 2002/0151599 A1 | 10/2002 | Buchholz et al. |
| 2003/0157205 A1 | 8/2003 | Jensen et al. |
| 2003/0190381 A1 | 10/2003 | Bland et al. |
| 2004/0048919 A1 | 3/2004 | Dreon et al. |
| 2004/0241261 A1 | 12/2004 | Prous et al. |
| 2005/0244522 A1 | 11/2005 | Carrara et al. |
| 2006/0083727 A1 | 4/2006 | Kajander et al. |
| 2006/0110468 A1 | 5/2006 | Liu et al. |
| 2006/0111308 A1 | 5/2006 | Robbins |
| 2006/0240037 A1 | 10/2006 | Fey et al. |
| 2007/0116838 A1 | 5/2007 | Prakash et al. |
| 2007/0190209 A1 | 8/2007 | Sinnott |
| 2008/0031940 A1 | 2/2008 | Rodriguez |
| 2008/0031980 A1 | 2/2008 | Rodriguez et al. |
| 2008/0045475 A1 | 2/2008 | Littmann |
| 2008/0095757 A1 | 4/2008 | Levin |
| 2008/0131534 A1 | 6/2008 | Jungbauer et al. |
| 2008/0181937 A1 | 7/2008 | Fotuhi |
| 2008/0234362 A1 | 9/2008 | Chandler |
| 2008/0286254 A1 | 11/2008 | Sakamoto et al. |
| 2009/0087501 A1 | 4/2009 | Cummins |
| 2009/0324703 A1 | 12/2009 | Frautschy et al. |
| 2010/0009038 A1 | 1/2010 | Ella et al. |
| 2010/0010005 A1 | 1/2010 | Lines |
| 2010/0130604 A1 | 5/2010 | Li et al. |
| 2010/0179103 A1 | 7/2010 | Desai |
| 2010/0260874 A1 | 10/2010 | Coral |
| 2011/0091580 A1 | 4/2011 | He et al. |
| 2011/0111055 A1 | 5/2011 | Lang |
| 2011/0111069 A1 | 5/2011 | Morre |
| 2011/0165099 A1 | 7/2011 | Arvanitidou et al. |
| 2011/0165291 A1 | 7/2011 | Loblaw et al. |
| 2011/0229537 A1 | 9/2011 | Matravers et al. |
| 2011/0305779 A1 | 12/2011 | Cowan |
| 2012/0052126 A1 | 3/2012 | Pathak et al. |
| 2012/0071550 A1 | 3/2012 | Zelkha et al. |
| 2012/0177758 A1 | 7/2012 | Minami et al. |
| 2012/0201884 A1 | 8/2012 | Gokaraju et al. |
| 2012/0207862 A1 | 8/2012 | Morre et al. |
| 2012/0237455 A1 | 9/2012 | Trivedi et al. |
| 2012/0237590 A1 | 9/2012 | Helson |
| 2013/0071369 A1 | 3/2013 | Mastaloudis et al. |
| 2013/0084253 A1 | 4/2013 | Brading et al. |
| 2013/0095095 A1 | 4/2013 | Lines |
| 2013/0156870 A1 | 6/2013 | Heller et al. |

FOREIGN PATENT DOCUMENTS

| | | |
|---|---|---|
| WO | 9634534 | 11/1996 |
| WO | 0149285 | 7/2001 |
| WO | 2004105714 | 12/2004 |
| WO | 2005077393 | 8/2005 |
| WO | 2005082407 | 9/2005 |
| WO | 2006067796 | 6/2006 |
| WO | 2006079109 | 7/2006 |
| WO | 2012035480 | 3/2012 |
| WO | 2012037311 | 3/2012 |
| WO | 2012037328 | 3/2012 |
| WO | 2012049253 | 4/2012 |
| WO | 2012050895 | 4/2012 |
| WO | 2012123962 | 9/2012 |
| WO | 2013016257 | 1/2013 |
| WO | 2013054267 | 4/2013 |

OTHER PUBLICATIONS

International Search Report, PCT/US2013/071597, Jun. 25, 2014.
Natalie A. Kelsey et al: "Nutraceutical Antioxidants as Novel Neuroprotective Agents", vol. 15, No. 11, Nov. 2010, pp. 7792-7814.
Invitation to Pay Additional Fees and Partial International Search for International Application No. PCT/US2013/071597, dated Feb. 26, 2014.
English language abstract and machine-assisted English translation for CN101356974 A extracted from http://worldwide.espacenet.com on Jul. 22, 2016, 8 pages.
Chinese Search Report, (English translation) May 18, 2016, 2 pages.
Cui Yu, "Research progress on Nrf2/ARE pathway and mechanism of antioxidation", Journal of Jilin University (Medicine Edition), vol. 37 No. 1, pp. 187-190.
English abstract for Cui Yu, "Research progress on Nrf2/ARE pathway and mechanism of antioxidation", Journal of Jilin University (Medicine Edition), vol. 37 No. 1, pp. 187-190.
Sui Hongwei, "Development research and application prospect of natural anti-oxidants", Journal of Wuhan Commercial Service College, vol. 20 No. 3.
English abstract for Sui Hongwei, "Development research and application prospect of natural anti-oxidants", Journal of Wuhan Commercial Service College, vol. 20 No. 3.
Manthana Bhairava, Anandakandah-Edited with Tamil translation by S.V. Radhakrishna Sastri, Tanjore, p. 6 (p. 04-09) ( Ref.pg. No.of publication:148 ), Edn. 1st 1952, T.M.S.S.M. Library, Madras, India.†
Rasatantrasarah Evam Siddhaprayogasasamgrahah, p. 5 (p. 10-14) ( Ref.pg. No.of publication:273 ), Edn 8th;1990, Krishan Gopal Ayurveda Bhawan, India.†
Trimalla Bhatta, Yogatrangini, p. 6 (p. 15-20) ( Ref.pg. No.of publication:63 ), 2003, Chaukhamba Vidyabhavan, Varanasi, India.†

\* cited by examiner
† cited by third party

ANTIOXIDANT DIETARY SUPPLEMENT AND RELATED METHOD

SEQUENCE LISTING

The subject application contains a Sequence Listing which has been submitted electronically in ASCII format and is hereby incorporated by reference in its entirety. Said ASCII copy, created on Apr. 13, 2016, is named 018716_150980_US_SL.txt and is 541 bytes in size.

BACKGROUND OF THE INVENTION

The present disclosure relates to supplements and methods for administration, and more particularly, to dietary supplements comprising a blend of turmeric, quercetin and rosemary or holy basil, wasabi and broccoli seed extract in specific ratios that can stimulate the Antioxidant Response Element (ARE) or Quinone Reductase (QR) and/or induce related gene expression, for example, heme oxygenase-1 (HMOX-1) expression.

Free radicals play a significant role in the onset and progression of a variety of conditions and diseases, for example, inflammation, allergic reactions, joint deterioration, arthritis, osteoporosis, cardiovascular diseases, cancer and the like. More particularly, in one example, it is believed that free radical damage to lipid molecules many cause low density lipoprotein peroxidation and initiate arterial plaque, which can lead to cardiovascular disease and atherosclerosis. In another example, free radical damage to protein molecules can cause alteration to tissue structure and immunological disorders, which can lead to arthritis and connective tissue damage that can alter the appearance and function of skin. Accordingly, much attention has been focused on the addition of antioxidants to dietary supplements and foods in order to scavenge free radicals in biologic systems.

A variety of compositions have been identified as having antioxidant capabilities. For example, curcumin from turmeric, a spice, has been shown to be an antioxidant and anti-inflammatory, both in vitro and in vivo. Some studies, focused on exposing bovine aortic endothelial cells to curcumin, indicate that curcumin is a potent inducer of HMOX-1 in such endothelial cells, and that it increased heme oxygenase activity. Motterlinin R et al, Curcumin, an antioxidant and anti-inflammatory agent, induces heme oygenase-1 and protects endothelial cells against oxidative stress. Free Radic Biol Med, April 15; 28(8):1303-12 (2000). However, these studies have not harnessed the full capabilities of curcumin.

Other unrelated attempts have been made to combine curcumin with other ingredients, such as quercetin and rosemary, to ameliorate specific inflammation related disease. For example, U.S. Pat. No. 6,210,701 to Darland, which is hereby incorporated by reference, combines curcumin, quercetin and rosemary in a ratio of about 2:1:2 to ameliorate such disease. This reference also provides that in this ratio, the observed Oxygen Radical Absorption Capacity (ORAC) of this ratio of combined ingredients has a better outcome than the ingredients individually with regard to ORAC. However, this reference does not contemplate whether the ORAC results would bear on or have a similar outcome concerning other functionality, such as ARE or HMOX-1 expression, nor does it even appreciate the effect of curcumin on these expressions. Indeed, the United States Department of Agriculture has recently removed their extensive ORAC database, reflecting the hypothesis that ORAC activity does not reflect the actual health benefit of samples. Therefore, there remains room for exploration and improvements in these areas.

SUMMARY OF THE INVENTION

A supplement and related method provide a formulation including a combination or blend of turmeric, quercetin and rosemary, which are present in a balanced and predetermined ratio, or a combination or blend of holy basil, wasabi, and broccoli seed extract in a predetermined ratio. The supplement stimulates the Antioxidant Response Element (ARE), Quinone Reducatse (QR) and/or induce related gene expression, for example, heme oxygenase-1 (HMOX-1) expression. This formulation and blend of ingredients can synergistically affect natural antioxidant response pathways within cells of a subject to whom the supplement is administered.

In one embodiment, the formulation is in the form of a dietary supplement in tablet, capsule or other forms that can be easily administered to a subject. The supplement can include the blend of turmeric, quercetin and rosemary, optionally along with other ingredients. The dietary supplement can be formulated so that the turmeric, quercetin and rosemary are present in the supplement in a predetermined ratio of 1:3:5.

In another embodiment, the dietary supplement including the blend of turmeric, quercetin and rosemary can be administered to cells or a subject. As a result of the administration, the blend can stimulate ARE in the cells or subject. ARE is a DNA sequence that is the binding site for the Nrf2 transcription factor. A primary mechanism in the cellular defense against oxidative stress is activation of the Nrf2 ARE signaling pathway. This pathway, and in particular Nrf2, controls the expression of genes whose protein products are involved in the impairment and reduction of reactive oxidative species via reactions and by enhancing cellular antioxidant capacity. Thus, the supplement can reduce oxidative stress and/or combat reactive oxidative species.

In even another embodiment, administration of the blend of turmeric, quercetin and rosemary can induce gene expression, such as HMOX-1 expression. In turn, cells with such expression can be induced to provide an antioxidant battery of protective enzymes, such as HMOX-1.

In yet another embodiment, a method of supplementing a human diet is provided, the method comprising: providing a supplement including the blend of turmeric, quercetin and rosemary, optionally along with other ingredients; and administering the supplement to the human, so as to supplement the diet of the human. Optionally, the human can be deficient in antioxidants, and in need of antioxidant supplementation. Further optionally, the human can be undergoing oxidative stress or exposed to reactive oxidative species.

The present invention provides a formulation having a blend of turmeric, quercetin and rosemary, optionally along with other ingredients, in a synergistic ratio, to stimulate ARE and/or induce HMOX-1 expression, which in turn can reduce oxidative stress and/or combat reactive oxidative species. Further, the supplement can improve antioxidant and nutrient status, minimize free radical damage, and can be used to ameliorate diseases and conditions associated with the same.

In one embodiment the blend of the turmeric, quercetin and rosemary are present in a ratio sufficient to decrease one of a urinary level of 8-isoprostane in a human and a blood serum level of catalase.

In one embodiment the blend of turmeric, quercetin and rosemary are present in a ratio sufficient to increase production of one of glutathione peroxidase and Superoxide dismutase in a human.

In one embodiment, the formulation is in the form of a dietary supplement in tablet, capsule or other forms that can be easily administered to a subject. The supplement can be a blend of holy basil, wasabi, and broccoli seed extract, optionally along with other ingredients. The formulation can be prepared so that the holy basil, wasabi, and broccoli seed extract are present in the supplement in a predetermined 1:1:0.2 ratio.

In another embodiment, a blend for inclusion in a dietary supplement, may include holy basil, wasabi, and broccoli seed extract, wherein the holy basil, wasabi, and broccoli seed extract are present in the supplement in an amount and in a ratio sufficient to at least one of stimulate Quinone Reductase activity and induce HMOX-1 expression when the supplement is administered to a subject.

In one embodiment, the blend of holy basil, wasabi, and broccoli seed extract are present in a ratio sufficient to decrease a urinary level of 8-isoprostane in a human.

In one embodiment, the blend of holy basil, wasabi, and broccoli seed extract are present in a ratio sufficient to increase Superoxide dismutase in a human.

In yet another embodiment, a method of supplementing a human diet is provided, the method comprising: providing a dietary supplement including holy basil, wasabi, and broccoli seed extract, wherein the holy basil, wasabi, and broccoli seed extract are present in the supplement in a ratio of 1:1:0.2; and orally administering the dietary supplement to a human so as to one of stimulate Quinone Reductase activity and induce HMOX-1 expression in cells of the human.

These and other objects, advantages, and features of the invention will be more fully understood and appreciated by reference to the description of the current embodiments and the drawings.

Before the embodiments are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENTS

Figure 1:
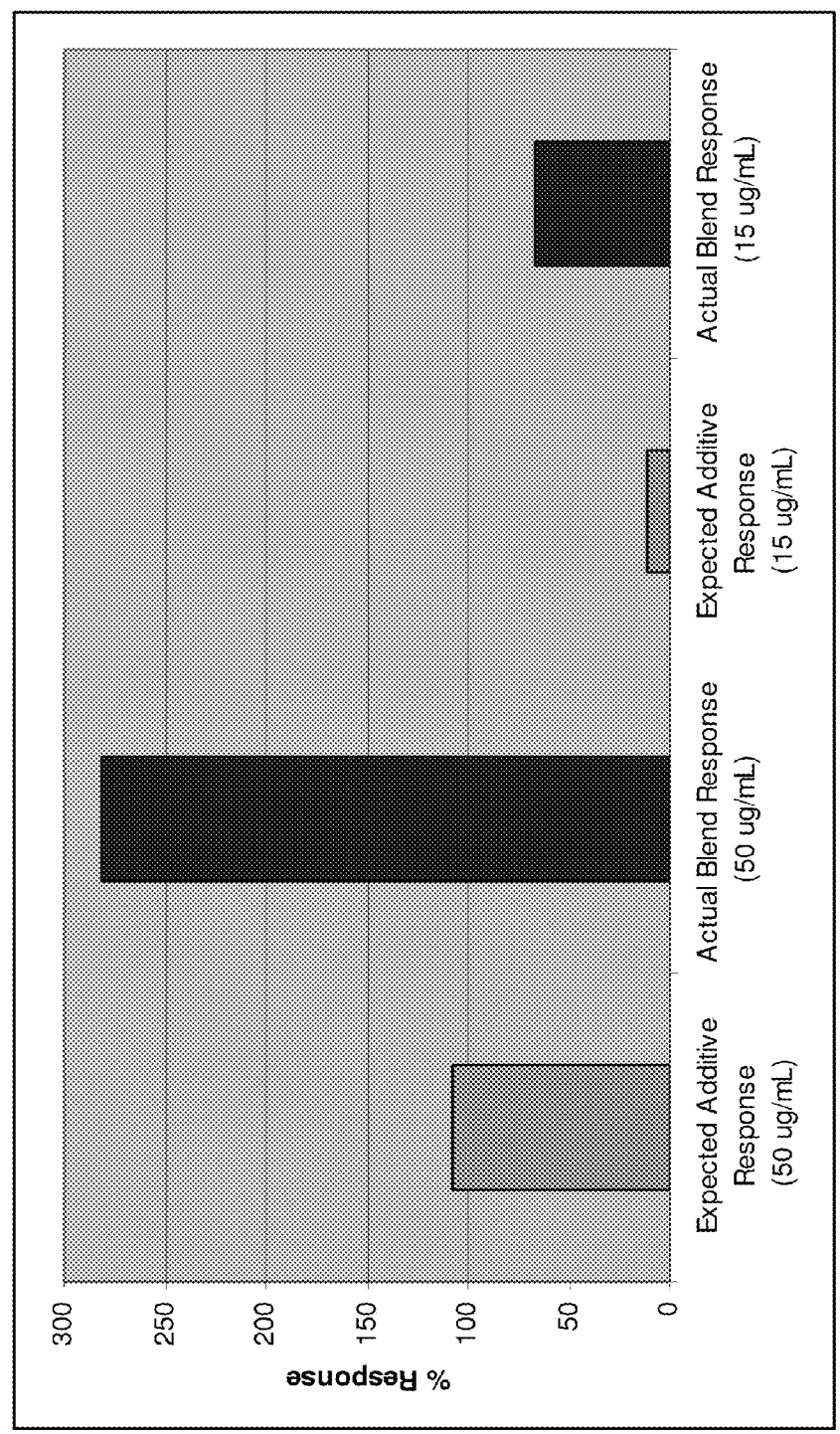
FIG. 1 is a graphical illustration of a synergistic effect of a blend of turmeric, quercetin and rosemary versus the expected additive effect of the blend in an ARE assay at different concentrations.

The current embodiment provides a formulation including a combination or blend of turmeric, quercetin and rosemary. The turmeric, quercetin and rosemary can be present in the blend, and generally in the formulation, in a ratio of 1:3:5. Alternatively, the formulation may include holy basil, wasabi, broccoli seed extract present in a ratio of 1:1:0.2. The formulation itself can be incorporated into a dietary supplement suitable for administration to a subject, such as a human or other mammal, in a variety of delivery vehicles as described below. The blend in its rudimentary form also can be incorporated into a delivery vehicle, such as a solution or concentration, suitable for in vitro testing or applications.

The turmeric, quercetin and rosemary can come from a variety of sources. For example, the turmeric can be derived, extracted or otherwise obtained from *Curcuma longa*, which is a rhizomatous herbaceous perennial plant of the ginger family, Zingiberaceae. Other Zingiberaceae plant materials can be substituted in certain situations for the *Curcuma longa*. The turmeric can be present in the formulation and/or blend in varying amounts. For example, the turmeric can be present in a weight percent range of the formulation or dietary supplement having a lower limit of any of the following: 1%, 2%, 3%, 4% or 5% and a corresponding upper limit of any of the following: 12%, 15%, 17% or 20%. As a further example, the turmeric can be present in a milligram weight range of the formulation or dietary supplement having a lower limit of any of the following: 10 mg, 20 mg, 30 mg, 40 mg or 50 mg, and a corresponding upper limit of any of the following: 130 mg, 140 mg, 150 mg, 160 mg or 170 mg.

The quercetin can be derived, extracted or otherwise obtained from a variety of fruits, vegetables and herbs, such as citrus fruits, apples (for example, *Malus domestica*), onions (such as, but not limited to, *Allium cepa*), parsley, sage, tea, blueberries, blackberries, bilberries, Fava d'anta (for example, *Dimorphandra mollis*) and *Sophora japonica*. The quercetin can be present in the formulation and/or blend in varying amounts. For example, the quercetin can be present in a weight percent range of the formulation or dietary supplement having a lower limit of any of the following: 3%, 4% or 5%, and a corresponding upper limit of any of the following: 33%, 35% or 40%. As a further example, the quercetin can be present in a milligram weight range of the formulation or dietary supplement having a lower limit of any of the following: 20 mg, 30 mg, 40 mg or 50 mg, and a corresponding upper limit of any of the following: 440 mg, 450 mg, 460 mg or 470 mg.

The rosemary can be derived, extracted or otherwise obtained from *Rosmarinus officinalis*, which is a herbaceous perennial plant of the mint family, Lamiaceae. Other Lamiaceae plant materials can be substituted in certain circumstances for the *Rosmarinus officinalis*. The rosemary can be present in the formulation and/or blend in varying amounts. For example, the rosemary can be present in a weight percent range of the formulation or dietary supplement having a lower limit of any of the following: 4%, 5%, 6% or 7%, and a corresponding upper limit of any of the following: 45%, 50%, 55% or 60%. As a further example, the rosemary can be present in a milligram weight range of the formulation or dietary supplement having a lower limit of any of the following: 45 mg, 50 mg, 55 mg or 60 mg, and a corresponding upper limit of any of the following: 740 mg, 750 mg, 760 mg or 770 mg.

The holy basil, wasabi, and broccoli seed extract can also come from a variety of sources. Holy basil, can be derived, extracted or otherwise obtained from the plant *Ocimum sanctum* in the Lamiaceae family and may also be known as Tulsi or tulasī. Other basils, such as but not limited to, sweet basil (*Ocimum basilicum*) may be substituted in certain circumstances for holy basil. Holy basil may be obtained from several sources including Verdure Sciences, Noblesville, Ind.

Wasabi material may be derived from *Wasabia japonica* as a pure rhizome dried powder. *Wasabia* is a member or the Brassicaceae family which includes cabbages, horseradish, and mustard. Other botanical materials from the Brassicaceae family may be substituted in certain circumstances for *Wasabia japonica*. Wasabi powder may be obtained from a variety of sources including B&D Nutritional Ingredients, Vista, Calif.

Extract from *Brassica oleracea italica*, or broccoli seed extract, originate from plants in the Brassicaceae family. The broccoli seed extract may be standardized to 13% glucoraphanin, a glucosinolate; and precursor of sulforaphane which is an isothiocyanate. *Brassica oleracea* is a species that includes cabbage, broccoli, cauliflower, kale, Brussel sprouts, savoy, and Chinese kale. Under certain circumstances, other botanical materials from the Brassicaceae family may be substituted for broccoli seed. Broccoli seed extract may be obtained from B&D Nutritional Ingredients, Vista, Calif.

These blends can be admixed in the formulation in a variety of manners. For example, where the formulation includes other ingredients as described below, the blend can be admixed directly with those other ingredients, generally homogeneously throughout the formulations, in whatever physical form it may take. Of course, sometimes, the blend can be premixed and added to other ingredients to produce the formulation. If desired, the ingredients of the blend can be agglomerated in a microcapsule, coating or other structure within the other ingredients.

The formulation, as mentioned above, can be included in dietary supplements. The supplements can be in the form of tablets, powders, gels, or liquids (a tablet, for the purposes of the present invention and as used throughout the application disclosure, refers to any form of a solid oral dosage, including but not limited to tablets, caplets, capsules, powders, etc.). The supplement can be formulated as a powder for mixing with consumable liquids such as milk, juice, water, or consumable gels or syrups for mixing into other dietary liquids or foods. The supplement also can be formulated with other foods or liquids to provide pre-measured supplemental foods, for example, single-serving bars. Flavors, excipients, binders, protein, complex carbohydrates, preservatives, chelating agents, and the like can be added depending on the application.

When implemented in a dietary supplement, the formulation can be administered in one or more tablets, administered twice a day. Of course, if desired, the dietary supplement can be administered in other forms and unit dosages as desired.

The dietary supplement can be formulated using any pharmaceutically acceptable form of other ingredients, for example, concentrates, phytochemicals, vitamins, minerals, and other nutrients, including salts and derivatives thereof. For example, suitable vitamins for use in the formulation and supplement can include vitamin A, vitamin B1, vitamin B2, vitamin B6, vitamin B12, niacin/niacinamide, pantothenic acid, folic acid, biotin, choline, vitamin C, vitamin D and vitamin E, optionally derived from plant and other natural sources. In addition to the vitamins listed above, minerals for use in the formulation and supplement can include boron, calcium, chromium, copper, iodine, magnesium, manganese, molybdenum, potassium, selenium, vanadium and zinc. Other vitamins and minerals may also be used.

Optionally, the formulation and in particular the blends described herein can be administered to a human, subject or biologic system that is identified as being or is prone to being deficient in antioxidants and related nutrients, that is prone to be or is undergoing oxidative stress, that has been subjected to reactive oxidative species and/or that is prone to or confirmed to have a disease and condition associated with the same. Further optionally, a subject can undergo conventional testing to assess whether the subject would benefit from the administration of the formulation as needed, or the formulation can simply be administered as a course of a regular supplement regimen.

The formulation of the current embodiment is illustrated in, but not intended to be limited by, the following examples.

EXAMPLE 1

The formulation including the blend of turmeric, quercetin and rosemary (TQR Blend, also referred to herein as Blend A) was tested to evaluate the ARE of the blend. In particular, the three individual ingredients, turmeric, quercetin and rosemary were tested by themselves and in combination as a blend. In the testing, a conventional assay for determining ARE was utilized. Generally, the assay included the human hepatocyte cell line HepG2 obtained from ATCC of Manassas, Va. that was stably transfected with a vector. The vector contained four repeats of the ARE DNA sequence (5'-GTGACTCAGCA-3' (SEQ ID NO: 1)) upstream of a minimal promoter using the firefly luciferase gene as a reporter. These cells were then treated with the individual ingredients turmeric, quercetin and rosemary, and the TQR Blend in varying concentrations for 48 hours in this and the other noted examples below. The human hepatocytes were lysed, the luciferase substrate, purchased from Biotium of Hayward, Calif., added, and the relative luminescence values were obtained for all samples. The results are shown as a % Response vs. Control. The control substance was sulforaphane at 10 µM.

Generally, the results indicate that the combined TQR Blend (Blend A) treatment induced significantly higher ARE activity than the expected additive activity of the individual ingredients, even at different concentrations. For example, as shown in FIG. 1 the expected additive response was calculated by summing the % Response for each of the ingredients when each was tested alone. If no synergy was occurring, it was estimated that the actual blend % Response would be approximately equal to the additive % Response. However, a response of 3-5 times higher than expected was observed in the blend treatment in both concentrations tested, that is, 15 µg/ml and 50 µg/ml. As a result, it was concluded that the three ingredients, turmeric, quercetin and rosemary, were working synergistically to activate the ARE in the TQR Blend.

Figure 2:
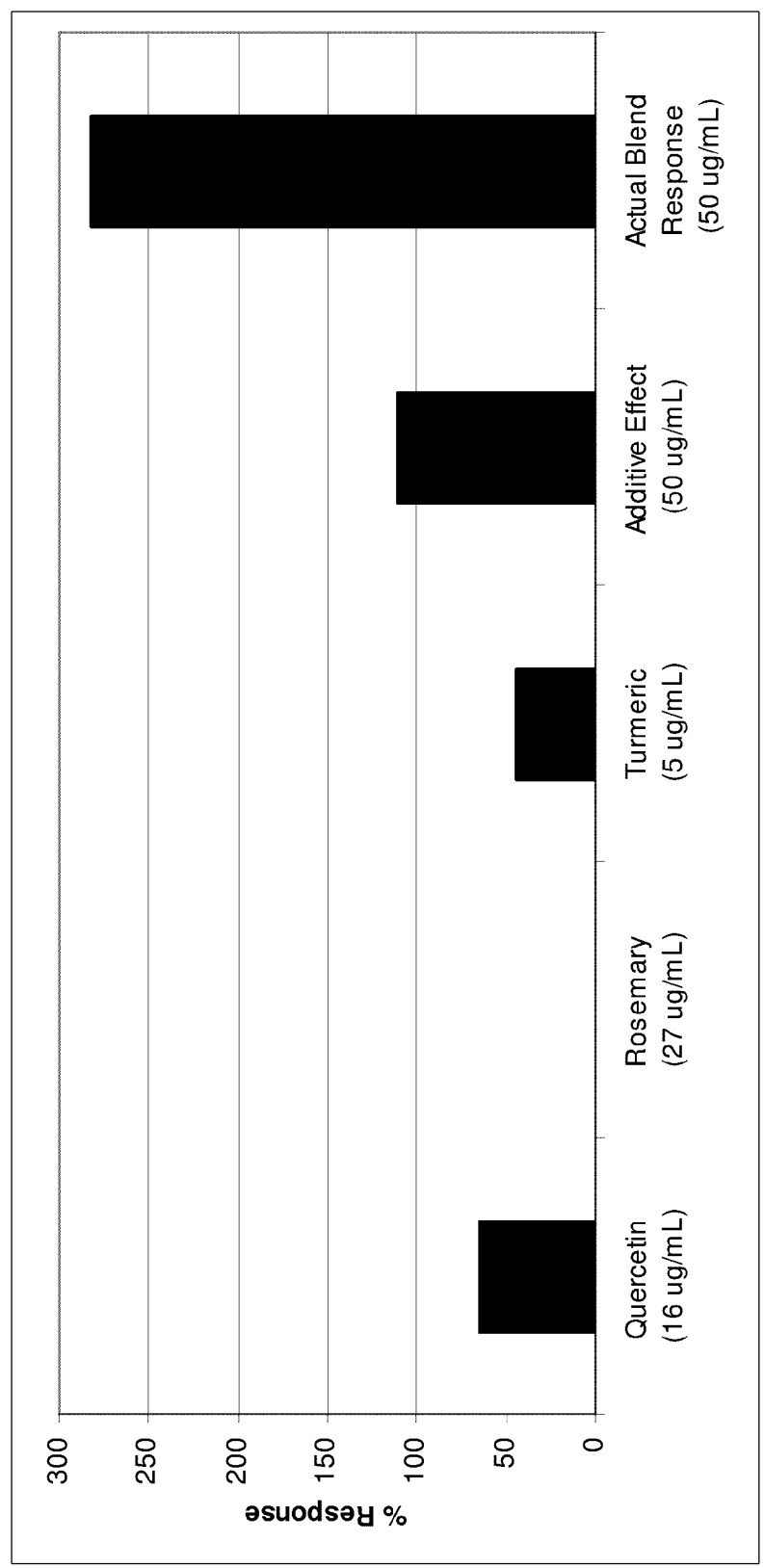
FIG. 2 is a graphical illustration of a synergistic effect of the blend of turmeric, quercetin and rosemary versus the expected additive effect of the blend and the effect of the individual ingredients of tumeric, quercetin and rosemary in the ARE assay.

As shown in FIG. 2, each of the three ingredients turmeric, quercetin and rosemary were tested individually, as well as in combination in the TQR Blend on the ARE assay. The actual TQR Blend % Response at the 50 µg/ml concentration was significantly higher, nearly 2.5 times more than the expected Additive Effect % Response at the 50 µg/ml concentration, which was simply calculated by adding the turmeric, quercetin and rosemary % Responses, taking into account their fraction by weight. This again confirmed that the TQR Blend had a synergistic effect on the ARE.

EXAMPLE 2

Figure 3:
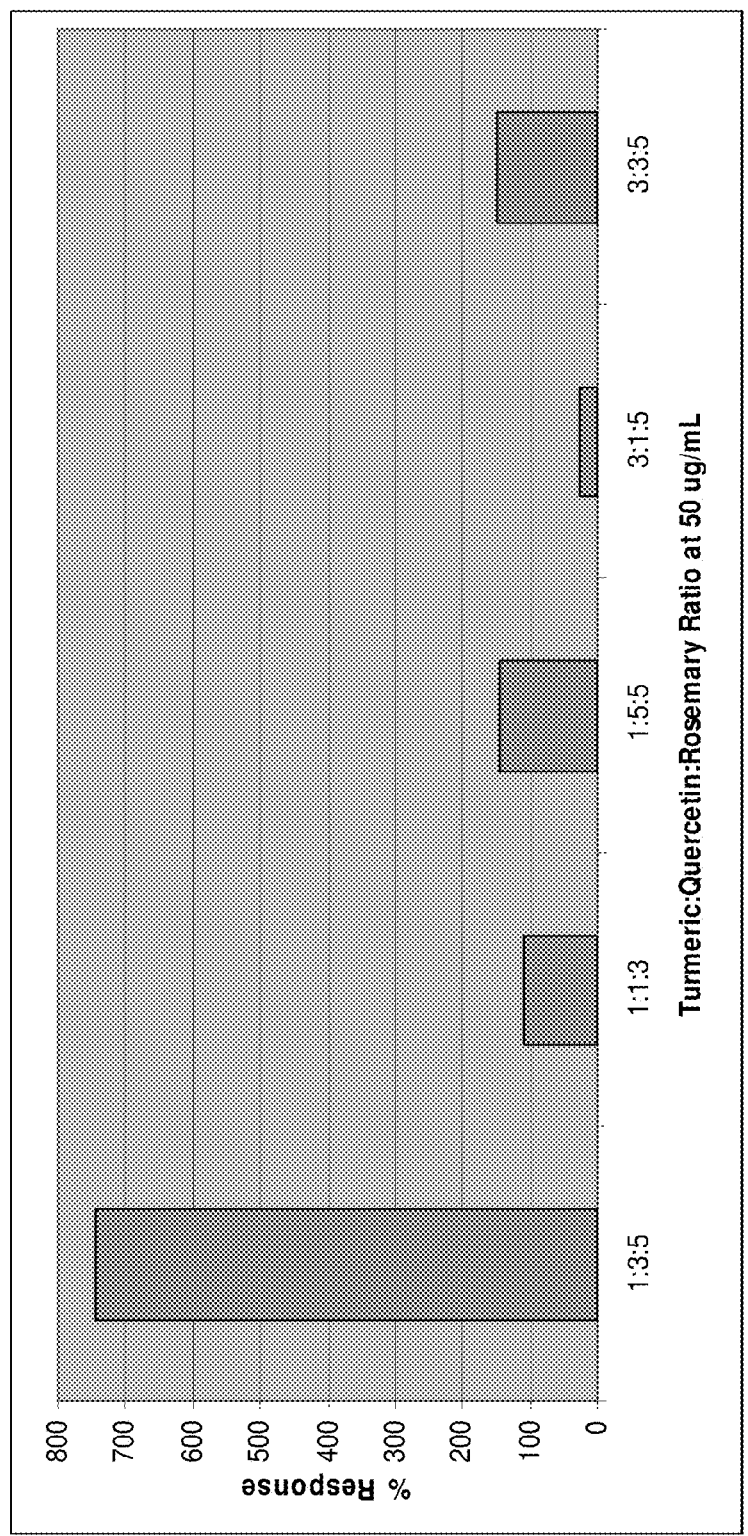
FIG. 3 is a graphical illustration of a synergistic effect of the blend of turmeric, quercetin and rosemary in various ratios in the ARE assay.

The formulation including the blend of turmeric, quercetin and rosemary, that is, the TQR Blend (Blend A), was tested to identify and discover a synergistic ratio of the ingredients. In particular, multiple ratios of turmeric:quercetin:rosemary were tested on the ARE assay of Example 1 to determine the most synergistic combination. All blends were tested at a concentration of 50 µg/mL. As shown in FIG. 3, it was discovered that the most synergistic ratio tested in the TQR Blend included turmeric, quercetin and rosemary at a ratio of 1:3:5. This was unexpected, as it previously appeared that the higher relative level of turmeric in the ratio should improve the overall synergy, but for some reason, the lower relative level of turmeric enhanced the synergy, perhaps because the turmeric may have been toxic for cells in culture at concentrations higher than 10-20 µg/ml.

EXAMPLE 3

Figure 4:
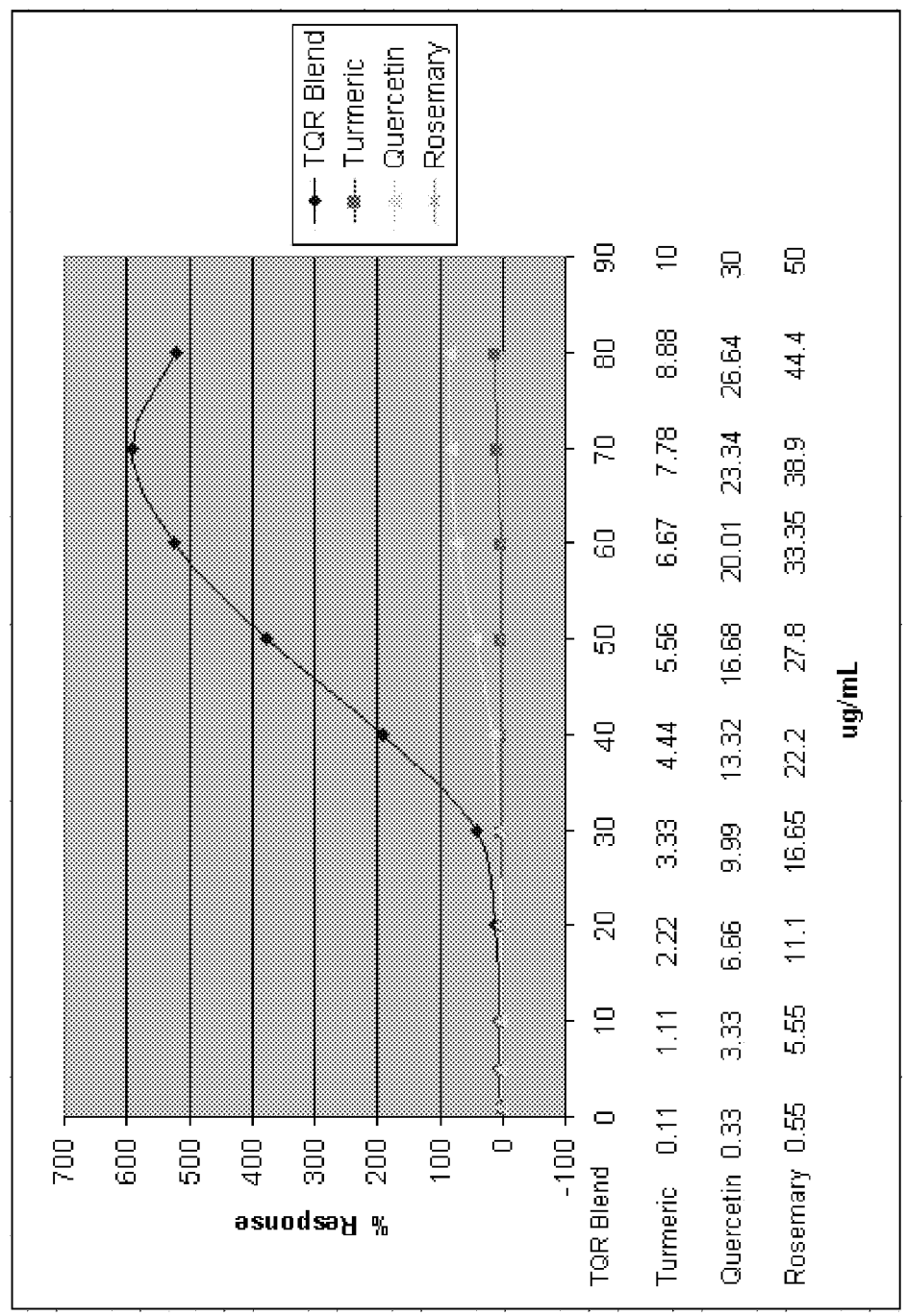
FIG. 4 is a graphical illustration of a synergistic effect of the blend of turmeric, quercetin and rosemary, as well as the individual ingredients, in various concentrations in the ARE assay.

The formulation including the blend of turmeric, quercetin and rosemary, that is, the TQR Blend (Blend A), was further tested to evaluate and verify the synergistic ratio of 1:3:5 at different concentrations of the ingredients. In particular, as shown in FIG. 4, varying concentrations in µg/ml of each of the individual ingredients of turmeric, quercetin and rosemary were tested in the ARE assay and compared to the corresponding concentrations in µg/ml of the TQR Blend with the ingredients at the 1:3:5 ratio at the different TQR concentrations. As a result of the testing, it was observed that when the TQR Blend had a concentration of 50 µg/ml at the 1:3:5 ratio of the turmeric, quercetin and rosemary, that TQR Blend had a % Response in the ARE assay that was at least 1, 2, 3, 4, 5, 6, 7, or 8 times greater than the corresponding % Response of any one of the turmeric, quercetin and rosemary individually at the noted concentrations. For example, quercetin exhibited about 50% Response, while the TQR Blend exhibited about 375% Response.

It was also observed when the TQR Blend had a concentration of 60 µg/ml at the 1:3:5 ratio of the turmeric, quercetin and rosemary, that TQR Blend had a % Response in the ARE assay that was at least 1, 2, 3, 4, 5, 6, or 7 times greater than the corresponding % Response of any one of the turmeric, quercetin and rosemary individually at the noted concentrations. For example, quercetin exhibited about 75% Response, while the TQR Blend exhibited about 525% Response.

It was additionally observed when the TQR Blend had a concentration of 70 µg/ml at the 1:3:5 ratio of the turmeric, quercetin and rosemary, that TQR Blend had a % Response in the ARE assay that was at least 1, 2, 3, 4, 5, 6, 7 or 7.5 times greater than the corresponding % Response of any one of the turmeric, quercetin and rosemary individually at the noted concentrations. For example, quercetin exhibited about 80% Response, while the TQR Blend exhibited about 600% Response.

It was further observed when the TQR Blend had a concentration of 80 µg/ml at the 1:3:5 ratio of the turmeric, quercetin and rosemary, that TQR Blend had a % Response in the ARE assay that was at least 1, 2, 3, 4, 5, 6 or 7 times greater than the corresponding % Response of any one of the turmeric, quercetin and rosemary individually at the noted concentrations. For example, quercetin exhibited about 90% Response, while the TQR Blend exhibited about 525% Response.

Figure 5:
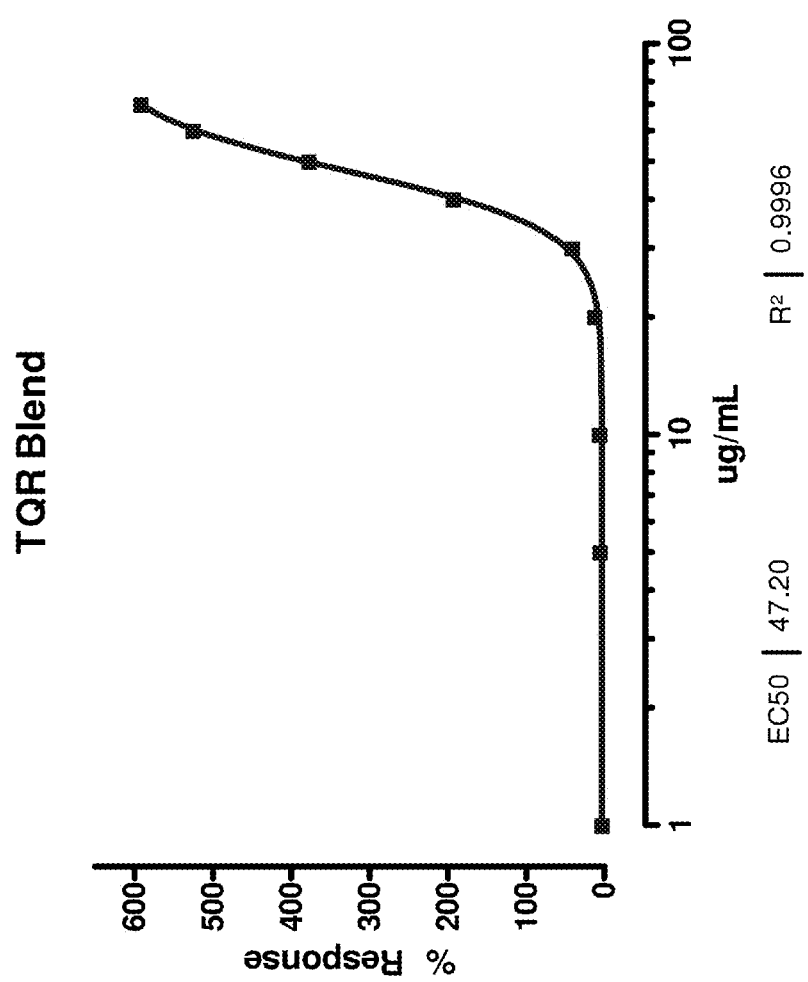
FIG. 5 is a graphical illustration of the EC50 value of the blend of turmeric, quercetin and rosemary.

Further testing showed that the TQR Blend activates the ARE in a dose-dependent manner. This is illustrated in the EC50 value chart in FIG. 5.

EXAMPLE 4

Figure 6:
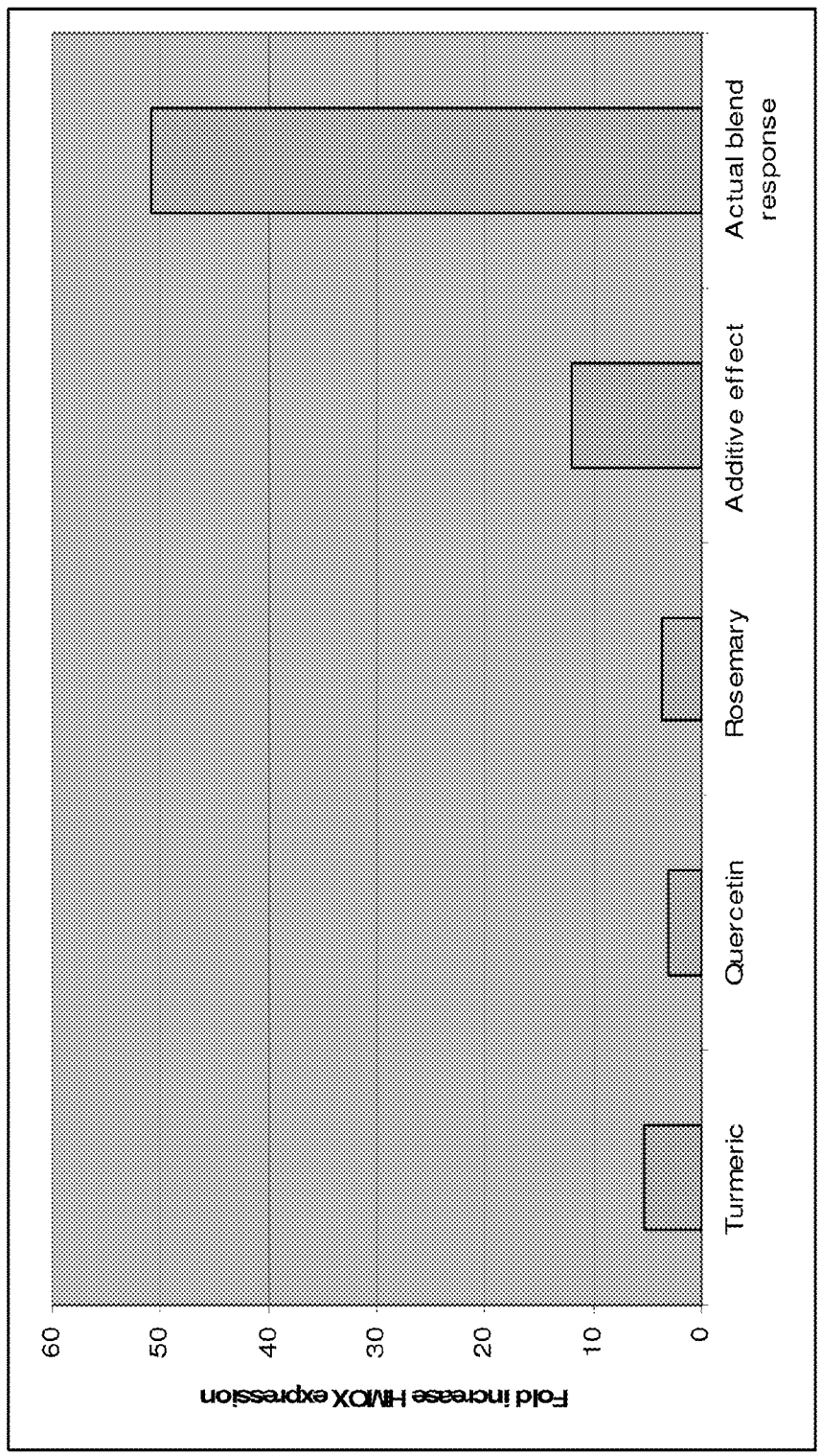
FIG. 6 is a graphical illustration of a synergistic effect of the blend of turmeric, quercetin and rosemary in a 1:3:5 ratio, as well as the effect of individual ingredients, on HMOX-1 gene expression.

To further test and verify the synergy exhibited in the above Examples, the effect of turmeric, quercetin, and rosemary individually, as well as the 1:3:5 ratio TQR Blend (Blend A) on gene expression of heme oxygenase-1 was assessed in a secondary assay. Generally, in the secondary assay, human breast carcinoma MCF-7 was treated with each of the turmeric (1.3 µg/ml), quercetin (3.9 µg/ml), and rosemary (6.5 µg/ml) individually, as well as the TQR Blend (15 µg/ml) overnight. The following day, mRNA was isolated from the treated cells and 2 step RT-qPCR was performed. The results illustrated in FIG. 6 demonstrate that each of the ingredients induced a greater than 3 fold increase in HMOX-1 expression in these cells. If all of these were added together, the additive effect might be expected to be approximately 11.9 fold. The actual response of the TQR Blend, however, was a fold increase of 50.9. Based on this, it is estimated that the response of the TQR Blend is at least 2, 3, 4 or 5 times greater than the HMOX-1 expression response of the additive effect of the tumeric, quercetin or rosemary.

EXAMPLE 5

Figure 7:
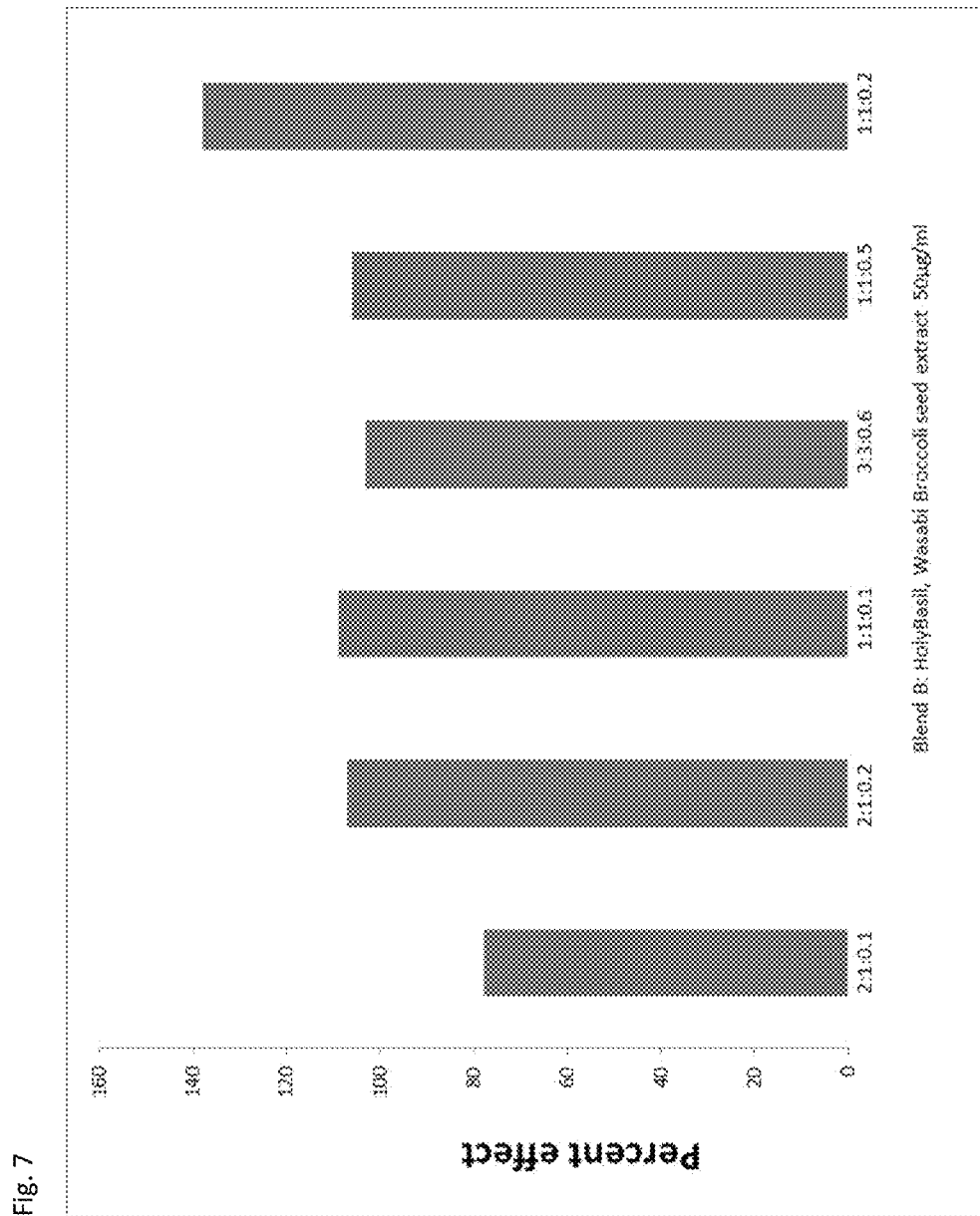
FIG. 7 is a graphical illustration of the effect of the blend holy basil, wasabi and broccoli seed with 50 µg at different ratios.

The formulation including the blend of holy basil, wasabi and broccoli seed (Blend B) was tested to evaluate its ability to induce Quinone Reductase (QR) enzyme (Phase II). QR is an enzyme whose activity is up-regulated by the same signals that up-regulate ARE. In particular, these three materials were tested by themselves and in combination as a blend at varying ratios including holy basil:wasabi:broccoli seed extract at 2:1:0.1, 2:1:0.2, 1:1:0.1, 3:3:0.6, 1:1:0.6, 1:1:0.5, and 1:2:0.2. In the testing, a conventional assay for determining QR activity was utilized. Generally, the assay included the mouse hepatocyte cell line Hepa1c1c7 obtained from ATCC of Manassas, Va. These cells were then treated with the individual materials holy basil, wasabi, and broccoli seed and the blend in varying ratios for 48 hours in this example. The mouse hepatocytes were lysed, and the QR substrate containing Glucose 6 phosphate, Flavin adenine dinucleotide ("FAD"), Nicotinamide adenine dinucleotide phosphate ("NADP"), glucose 6 phosphate dehydrogenase, MTT and menadione were added and incubated for 3-4 minutes at room temperature for purple color to develop (indicative of QR activity). The activity of QR was proportional to the absorption value at 610 nM. The results of the blend ratios are shown as a % Response vs. Control in FIG. 7. The control substance was sulforaphane at 1M.

Figure 8:
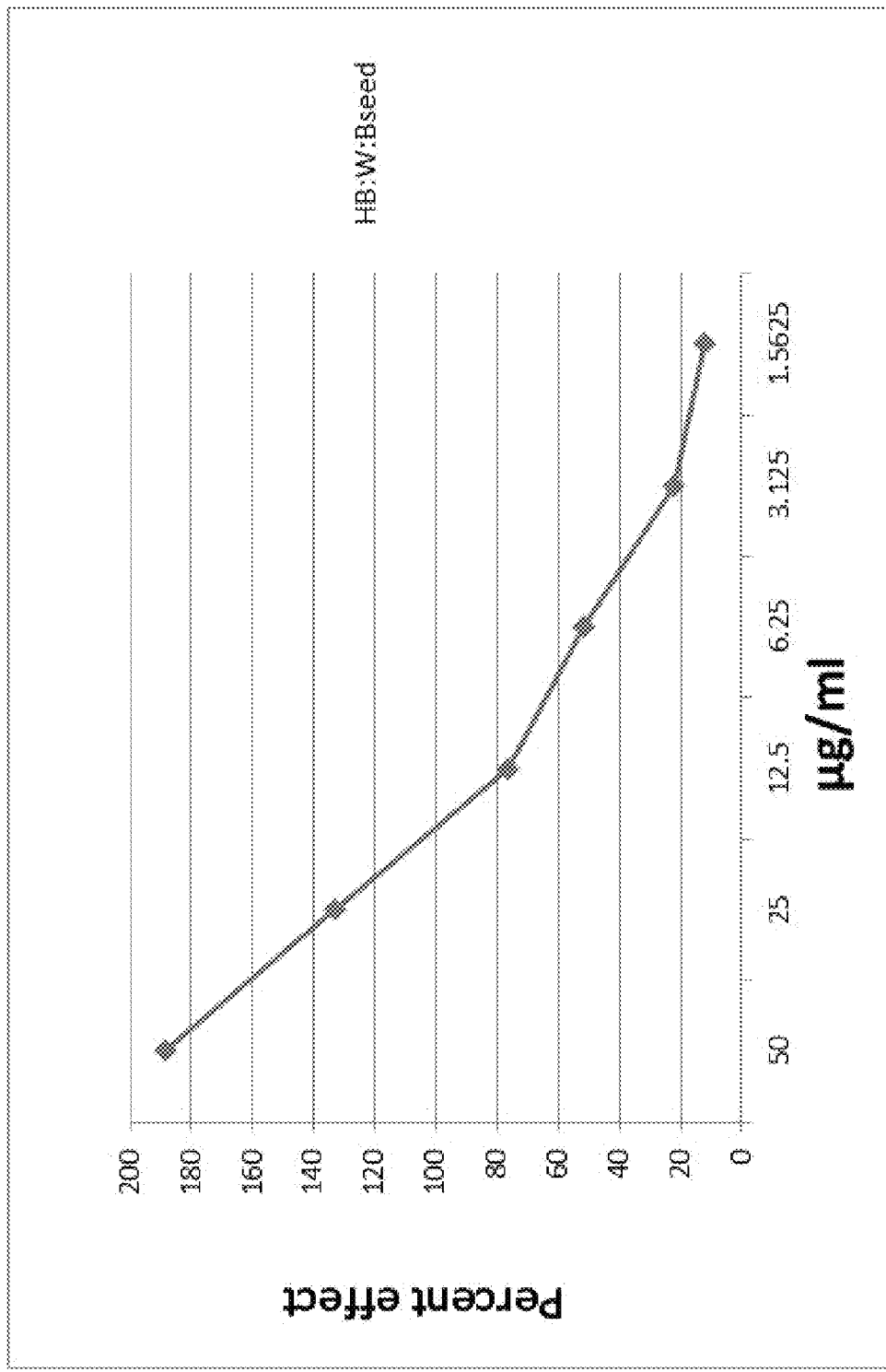
FIG. 8 is a graphical illustration of the dose dependent activation of Quinone Reductase (QR) of the blend holy basil, wasabi and broccoli seed at a ratio of 1:1:0.2.

The ratio of 1:1:0.2 of holy basil, wasabi and broccoli was selected for use in a clinical trial, discussed herein below. A dose dependent study of the activation of Quinone Reductase at this ratio was conducted and the results are shown in FIG. 8.

Figure 9:
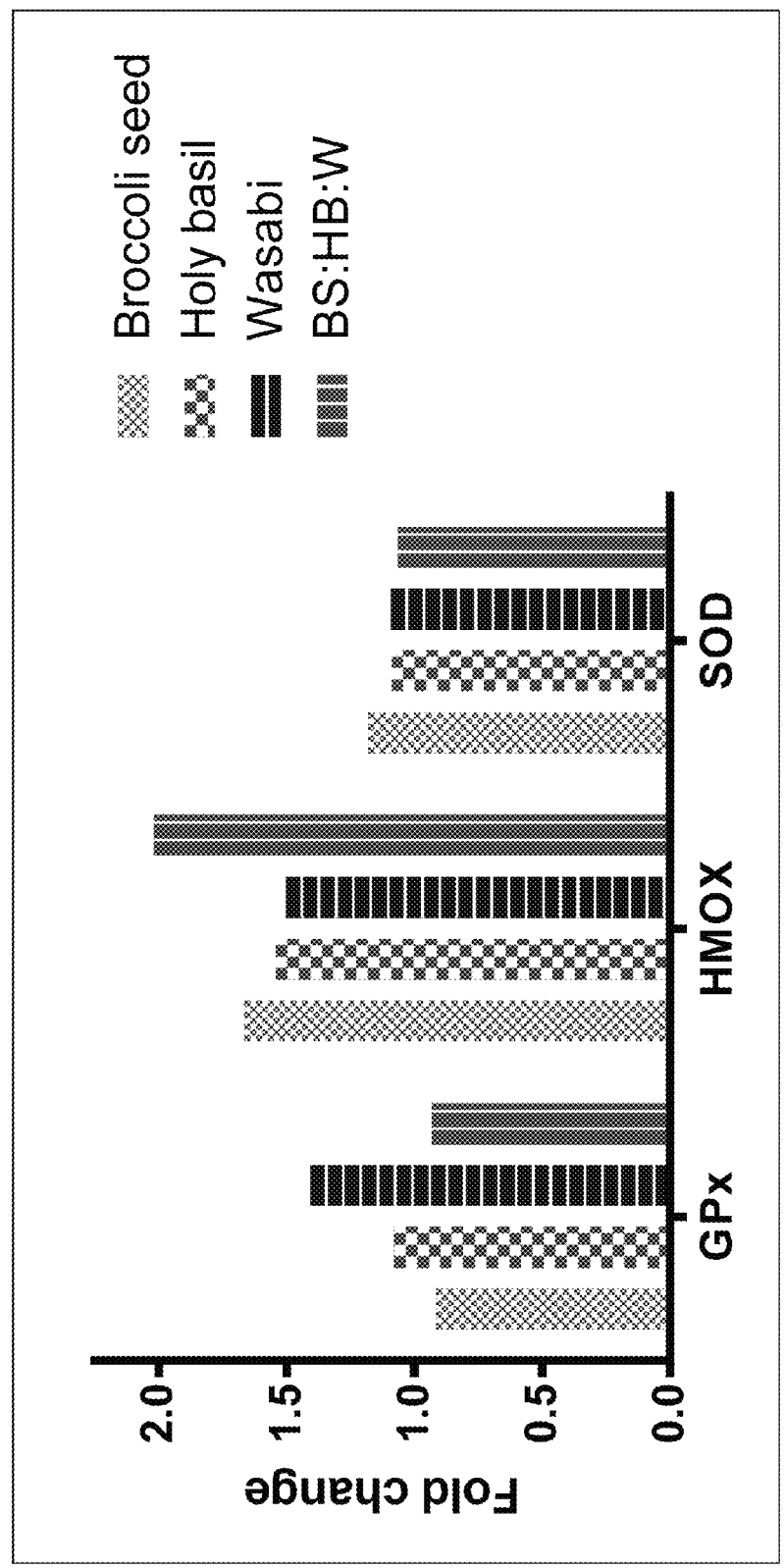
FIG. 9 is a graphical illustration of the effect of the blend holy basil, wasabi and broccoli seed on HMOX-1 gene expression.

The effect of Blend B (holy basil, wasabi, and broccoli seed extract) on Antioxidant Gene expression are shown in FIG. 9. Concentrations of 5 µg holy basil, 5 µg wasabi, and 1 µg broccoli seed extract were combined. RT-qPCR was performed. Each of the samples individually produced an approximate 1.5 fold induction of HMOX, as measured by the same method described with respect to Example 4, while the response was about 2 fold in the presence of all three.

Clinical Analysis

Four different plant based blends (Blends A, B, C and D) were prepared at two dosages each (300 mg and 600 mg). Sixty (60) healthy men were recruited to participate in the study. Participants were randomly divided into four groups so that fifteen (15) participants were assigned for each of the four blends. Results from participant groups selected to consume Blends A and B will be discussed further herein. Results from participant groups selected to consume Blends C and D do not relate to the current invention as Blends C and D contain material blends that are different from Blends A and B.

Given that aging is considered an oxidative stress model, a relatively older subpopulation was selected of participates aged between 45-65 years. Individual ethnic backgrounds were not considered. However, the participant candidate population at the Southbay Pharma Research site in Buena Park, Calif. comprise approximately 40% white, 20% Hispanic, 30% Asian/Pacific Islander, and 10% other. Women were excluded to avoid hormonal effects on the results. Participates were screened to exclude those with chronic diseases or major health issues. Further, participant candidates completed a Recommended Foods Checklist ("RFC") and a 62-item Food Frequency Questionnaire ("FFQ") to determine their individual level of consumption of foods recommended in current dietary guidelines. Participants showing a low fruit and vegetable intake were selected for further screening.

Some medications and foods may alter the level of oxidative stress biomarkers due to their ability to activate or suppress the Nrf2/ARE pathway. To avoid potential interference, such as false positive results, from common pharmaceuticals and foods, the following items were not allowed to be consumed by the participants for at least 10 hours prior to the blood and urine sample collection:

1. statins (e.g., simvastatin, fluvastatin) because they may activate or suppress the Nrf2/ARE pathway which will impact the ARE receptor;
2. NSAIDS, including aspirin;
3. Nitric oxide (eNOS) activators, including statins;
4. Selegiline because it may activate ARE;
5. PDE5 inhibitors such as Viagra® because it may activate ARE (demonstated up-regulation of HMOX-1 and increase in vascular NO);
6. Angiotensin II receptor blocker Telmisartan (for blood pressure); and
7. Capsaicin (spicy foods), coffee, tea and herbal teas because they may activate an ARE pathway.

Figure 10:
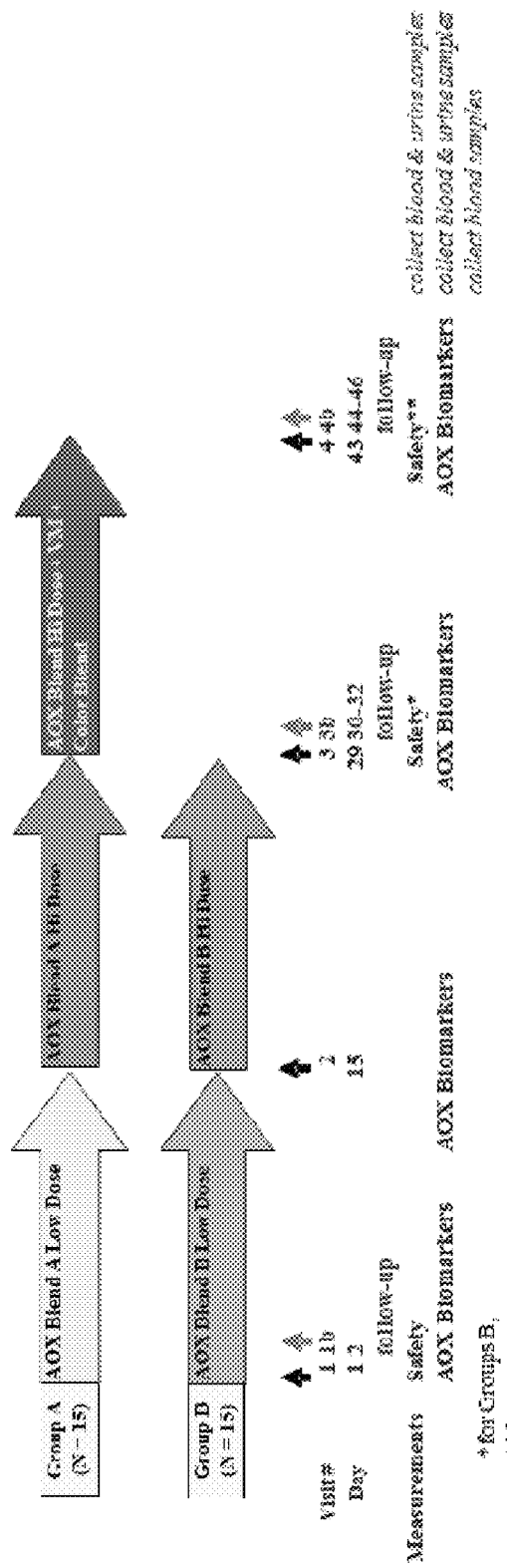
FIG. 10 is a schematic diagram of the time line for the clinical study.

After collecting basic health and medical information, the participants endured an overnight fast (at least 10 hours) after which blood and urine samples were collected to determine baseline levels of oxidative stress biomarkers and gene expression. Once the initial samples were collected, the participants were assigned to one of Groups A or B. A schematic chart summarizing the timeline of the study for each of the groups is shown in FIG. 10. Group A received a low dose of Blend A for 14 days, then a high dose of Blend A for 14 days, followed by 14 days of high dose Blend A plus a vitamin, mineral and color blend. Groups B received a low dose of Blend B for 14 days. Subsequent to the 14-day low dose phase, Groups B received a 14-day supply of high dose Blend B. Fasting blood and urine samples were collected from all participants at approximately 14-day intervals after completing a 14-day period and before progressing to the higher dose or added supplement if any were to follow. Further details with respect to the high and low dose of Blends A and B are shown in Table 1, below.

TABLE 1

Antioxidant Blends

| Arm | Level | Daily Dose (mg) | Content Per Day | Frequency |
| --- | --- | --- | --- | --- |
| AOX Blend A | Low | 300 | R/Q/T (5:3:1): Rosemary 167 mg, Quercetin 100 mg, Turmeric: 33 mg | morning (150 mg) & evening (150 mg) |
| AOX Blend A | High | 600 | R/Q/T (5:3:1): Rosemary 333 mg, Quercetin 200 mg, Turmeric: 67 mg | morning (300 mg) & evening (300 mg) |
| AOX Blend B | Low | 300 | HB/W/BS (5:5:1): Holy Basil 136 mg, Wasabi 136 mg, Broccoli seed 28 mg | morning (150 mg) & evening (150 mg) |
| AOX Blend B | High | 600 | HB/W/BS (5:5:1): Holy Basil 273 mg, Wasabi 273 mg, Broccoli seed 54 mg | morning (300 mg) & evening (300 mg) |

R/Q/T = Rosemary/Quercetin/Turmeric
HB/W/BS = Holy Basil/Wasabi/Broccoli seed

From the blood and/or urine samples collected, six biomarkers and/or gene expression levels were analyzed to determine the efficacy of each plant-based blend at stimulating an ARE and/or inducing related gene expression. The biomarkers/gene expression indicators analyzed were melondialdehyde, isoprostane, Superioxide dismutase, glutathione peroxidase, Heme Oxygenage-1 and catalase.

Melondialdehyde ("MDA") as measured by colormetric and spectrometric methods were analyzed. MDA may be a degradation product of polyunsaturated lipids generated from reactive oxygen species ("ROS") and is therefore a biomarker of oxidative stress state. MDA analysis was conducted by the following method:

Several solutions were prepared including:

TMOP=10 mM in 20 mM PBS buffer (exact TMOP concentration is determined by measuring absorbance at 532 nm after TBARS reaction with extinction coefficient of 156,000 M·cm−1 beforehand, typically not more than 6% from weight calculation). TMOP was used to dilute to 0.0, 0.2, 0.4 and 0.6 µg standard solutions with PBS.

BHT=Dissolve 0.5 grams BHT in 100 mL MeOH (0.0227 M).

TBA=Dissolve 0.5 g of TBA in ~80 mL of nanopure water. Shake vigorously and heat to ~50 oC if residue remains. Cool to room temperature if heated, dilute to 100.0 mL with nanopure water (0.5%).

TCA Dissolve 70 g TCA in nanopure water, dilute to a total volume of 100 mL with nanopure water (70%). Dilute part of 70% TCA with nanopure water to 10%.

Preparation for the MDA analysis also included labeling clean boil-proof microtubes for samples to be tested in triplicate and one for each standard. A VWR block dryer was turned on with the temperature set to 60° C. During the procedure, to a labeled boil-proof microtube, 15.0 µL of BHT solution was added to the bottom of the tube. 270.0 µL TMOP standard or plasma sample was added, 15.0 µL 10% TCA was added, 300.0 µL TBA solution was added in that order. The tubes were capped and solutions mixed. After all standards and samples were processed, the tubes were placed in the VWR dry block heater at the same time and incubated at 60° C. for 90 minutes. After cooling, 300.0 µL 70% TCA, then 900.0 mL chloroform were added and the samples were vigorously shaken, then centrifuged at 13,000 g for 3 minutes. The upper aqueous layer was transferred to a semi-micro cuvet and the UV-Vis spectrum was measured by scanning 430 to 630 nm.

UV-Vis spectra was converted to $3^{rd}$ derivative spectra. Values for $d^3A/dx^3$ were read at 542 nm for standards and samples. A standard curve was constructed from the standards and TBARS (MDA) concentrations were determined by using linear regression formulas.

Isoprostane is produced by a free radical-catalyzed mechanism and is a prostaglandin-like product of arachidonic acid peroxidation. Considering its free radical-dependent formation, isoprostane 8-iso $PGF_{2\alpha}$ is a biomarker that may reflect the whole body oxidative stress state.

Isoprostane 8-iso PGF2α was analyzed by Urinary Isoprostane ELISA Kit, Product number EA85 from Oxford Biomedical Research, Oxford, Mich. Prior to use of the ELISA Kit, the urine samples were normalized for creatinine to allow a reasonable sample to sample comparison. Creatinine urine concentrations were measured by the following procedure:

The following three solutions were prepared:

Picric Acid=Dry water-moistured picric acid under vacuum for 2 hours. Dissolve 9.156 g of picric acid in 1.0 L of nanopure water (filter if residue remains, 0.04M). Store in a brown bottle or wrapping the bottle with aluminum foil sheet, in the dark.

NaOH=Dissolve 30 grams NaOH in 1.0 L of nanopure water (0.75 N).

Creatinine=Dissolve 0.2645 g of ceatinine•HCl in 10.0 mL 1N HCl and 90.0 mL nanopure water (2.0 mg/mL creatinine). Dilute 1.0 mL of 2.0 mg/mL creatinine with 99.0 mL nanopure water (0.020 mg/mL creatinine). Store in a refrigerator. Dilute to make 0.0 mg/mL, 0.005 mg/mL, 0.010 mg/mL, 0.015 mg/mL and 0.020 mg/mL creatinine standards. Divide standards into small volumes and store in separate vials in a refrigerator.

Further preparation included labeling clean semi-micro cuvets (duplicates for each sample). Adding 1485.0 µL of nanopure water to each tube, adding 15.0 µL of samples into each tube, and capping and mixing the solution at 1/100× dilution of the urine sample. The dilution factor was adjusted if absorbance at 520 nm of the sample is outside the calibration range and the assay repeated. The procedure included adding 1.5 mL of nanopure water (triplicate, reagent blank) to a semi-micro cuvet or 1.5 mL of 1/100× urine sample or 1.5 mL of a standard solution. Then 0.5 mL of 0.75N NaOH was added to each cuvet, then 0.5 mL of 0.04M picric acid was added, then the samples were mixed well and incubated at room temperature for 30 minutes. The UV-Vis absorbance at 520 nm of each standard and sample were measured. Results were calculated by reading the absorbance values at 520 nm for standards and samples and subtracting the absorbance of the reagent blank. A standard curve was constructed from the standards and creatinine concentration in the samples was calculated by linear regression formulas. Then the dilution factor was applied (100 or other adjusted values).

Superoxide dismutases ("SODs") are antioxidant enzymes that are important to cells that are exposed to oxygen. SOD converts damaging superoxide to less harmful oxygen and hydrogen peroxide. SOD was measured with Human Cu/ZnSOD Platinum ELISA BMS222/BMS222TEN from eBioscience, Inc., San Diego, Calif.

Glutathione peroxidase ("GSH-Px") is an enzyme that protects the organism from oxidative damage caused by peroxides. More specifically, it reduces the harmful effects of lipid hydroperixides, free hydrogen peroxides, to less harmful compounds such as alcohols or water. This enzyme was measured with Bioxytech® GPx-340™ Colormetric Assay, Catalog Number 21017, Oxis Research, Portland, Oreg.

Heme Oxygenase-1 ("HMOX-1") is an essential enzyme that catabolizes heme to prevent it from causing oxidative stress. This enzyme cleaves heme to form a less harmful biliveridin. HMOX-1 was determined by use of HO-1 (human), EIA kit, catalog Number ADI-EKS-800, Enzo Life Sciences International, Inc., Plymouth Meeting, Pa.

Lastly, catalase is an enzyme important for cells exposed to oxygen because it protects the cells from oxidative damage caused by ROS. Catalase catalyzes the reactive hydrogen peroxides to non-harmful water and oxygen. Catalase was analyzed according to the Catalase Human ELISA Kit available from Abcam in Cambridge, Mass.

EXAMPLE 5

Blend A, containing rosemary, quercetin, and turmeric at a 5:3:1 ratio, was provided to Group A in two sequential dose levels (300 mg/day and 600 mg/day). After baseline blood and urine samples had been collected, fifteen participants were given low dose sample supplements each containing 150 mg of Blend A. Group A participants were instructed to consume the supplement twice daily and were recommended to consume the first part of the daily dose with a morning meal and the second part of the daily dose with an evening meal so as to consume a total of 300 mg/day of Blend A for 14 days. On Day 15, after an overnight (at least 10-hour) fast, blood and urine samples were collected. The same participants were then given a 14-day supply of high dose sample supplements each containing 300 mg of Blend A and were recommended to consume, beginning on Day 15, this supplement twice daily with the first part of the daily dose being consumed with a morning meal and a second part of the daily dose being consumed with an evening meal so as to consume a total of 600 mg/day of Blend A for 14 days.

On Day 29, after an overnight (at least 10-hour) fast, blood and urine samples were again collected. Group A participants were again given a 14-day supply of the high dose supplement to consume twice daily as recommended previously. In addition, Group A participants were given a vitamin, mineral and color blend containing the components shown in Table 2, below. Group A continued to consume the high dose supplement along with the vitamin, mineral and color blend supplement for 14 days. On approximately Day 43 and after an overnight (at least 10-hour) fast, blood and urine samples were again collected from Group A participants.

TABLE 2

Vitamins, Minerals and Color Blend Components

| | Daily Dose | Unit | Notes |
|---|---|---|---|
| Vitamins (unit) | | | |
| Total Retinol | 8333 | IU | |
| Vitamin A | 7083 | IU | |
| Beta-Carotene | 7083 | IU | From Carotenoid blend |
| B1 (Thiamine) | 4.5 | mg | |
| B2 (Riboflavin) | 5.1 | mg | |
| B3 (Niacin) | 20 | mg | |
| B5 (Pantothenic acid) | 10 | mg | |
| B6 (Pyridoxine) | 6 | mg | |
| B7 (Biotin) | 300 | mcg | |
| B9 (Folic Acid) | 800 | mcg | |
| B12 (Cyanocobalamin) | 12 | mcg | |
| Vitamin C | 250 | mg | |
| Acerola cherry | 20 | mg | From 100 mg of acerola cherry extract |
| Vitamin D | 1000 | IU | |
| Vitamin E (-tocopherols) | 30 | IU | |
| Tocotrienols | 4 | mg | |
| Vitamin K | 20 | mcg | |
| Choline | 55 | mg | |
| Minerals (unit) | | | |
| Calcium | 250 | mg | |
| Chromium | 120 | mcg | |
| Iodine | 150 | mcg | |
| Magnesium | 250 | mg | |
| Manganese | 2.0 | mg | |
| Molybdenum | 50 | mcg | |
| Selenium | 100 | mcg | |
| Zinc | 15 | mg | |
| Color Blend* | Daily Dose | Unit | Sources |
| Carotenoid Blend | 15.6 | mg | Containing a mixture of beta-carotene, alpha-carotene, zeaxanthin, lycopene, astaxanthin, and lutein |
| Astaxanthin beadlets (4%) | 1.5 | mg | |
| Citrus Bioflavonoid Complex as Yellow/Orange color | 40 | mg | Containing a mixture of contains: Sweet Orange, Grapefruit, Lemon, and Mandarin |
| Acerola cherry concentrate (20% vitamin C) - as Red color | 200 | mg | *Malpighia glabra* |
| Berry Blend - as Purple/Blue color | 50 | mg | Containing a mixture of blueberry (*Vaccinium corymbosum*), blackcurrant (*Ribes nigrum*), elderberry (*Sambucus nigra*), grape (*Vitis vinifera*) |
| Horseradish - as White color | 10 | mg | *Armoracia rusticana* |
| AWPS Complex - as Green color | 50 | mg | Containing a mixture of alfalfa (*Medicago sativa*), watercress (*Nasturtium officinale*), parsley (*Petroselinum crispum*), spinach (*Spinacia oleracea*); |
| Peppermint - as Green color | 30 | mg | *Mentha x piperita* |

*Recent America's Phytonutrient Report: Quantifying the Gap indicates that on average, 8 out of 10 Americans (76%) have a "phytonutrient gap." The "gap" represents the shortfall of phytonutrient intakes based on a typical level of phytonutrient intake consistent with a diet that is considered to have a prudent amount of fruits and vegetables. The rationale of the "color" portion of the blend is to bring the gap closer by providing fruits and vegetables from 5 color categories (green, red, white, purple/blue, and yellow/orange) according to the report.

EXAMPLE 6

Blend B, containing holy basil, wasabi and broccoli seed at a 5:5:1 ratio, was provided to Group B in two sequential dose levels (300 mg/day and 600 mg/day). After baseline blood and urine samples had been collected, fifteen participants were given low dose sample supplements each containing 150 mg of Blend B. Group B participants were instructed to consume the supplement twice daily and were recommended to consume the first part of the daily dose with a morning meal and the second part of the daily dose with an evening meal so as to consume a total of 300 mg/day for 14 days. On Day 15, after an overnight (at least 10-hour) fast, blood and urine samples were collected. The same participants were then given a 14-day supply of high dose sample supplements each containing 300 mg of Blend B and were recommended to consume, beginning on Day 15, this supplement twice daily with the first part of the daily dose being consumed with a morning meal and a second part of the daily dose being consumed with an evening meal so as to consume 600 mg/day of Blend B for 14 days. On day 29, after an overnight (at least 10-hour) fast, blood and urine samples were again collected.

Clinical Results

The differences between the biomarkers/gene expression levels detected in the samples collected from the participants were calculated from the baseline measurements. The changes from the baseline to the samples obtained after 14 days of consuming low dose supplement is designated as "L-BL". The difference in the detected values from the samples taken after the low dose phase and the samples taken after 14 days of the consuming a high dose supplement is designated as "H-L". For Group A there is another delta measured by determining the difference in samples after the 14 day period of high dose consumption and the 14 day period of the combination of the high dose supplement with vitamins, minerals and the color blend. This delta is designated "C-H".

Deltas were calculated and paired t-test was applied to compare changes in biomarkers between baseline and low dose (L-BL), low dose and high dose (H-L), and combination formula and high dose (C-H) (for Group A). Additionally, correlations between oxidative stress biomarkers were assessed and univariate statistics were estimated (p-values, heat map). The data were analyzed using the statistical analysis software JMP (SAS Institute). Treatments with most favorable treads and effects are highlighted in grey.

TABLE 3

Summary of Results

| Biomarker | Prod Code | Group | N | Mean (delta MDA spec) | Std Dev (delta MDA spec) | p-value |
|---|---|---|---|---|---|---|
| MDA colormetric, uM | A | L-BL | 15 | 1.333E-05 | 0.032 | |
| | A | H-L | 15 | 0.012 | 0.045 | |
| | A | C-H | 15 | 0.012 | 0.035 | |
| | B | L-BL | 15 | 0.006 | 0.049 | |
| | B | H-L | 15 | 0.002 | 0.035 | |
| MDA spectroscopy, uM | A | L-BL | 15 | 0.0054 | 0.024 | |
| | A | H-L | 15 | -0.0064 | 0.041 | |
| | A | C-H | 15 | 0.0104 | 0.032 | |
| | B | L-BL | 15 | 0.0144 | 0.029 | |
| | B | H-L | 15 | -0.0114 | 0.027 | |
| 8-isoprostane, ng/mL | A | L-BL | 15 | -1.800 | 2.255 | 0.004 |
| | A | H-L | 15 | 1.287 | 1.843 | |
| | A | C-H | 15 | -0.830 | 2.141 | 0.077 |
| | B | L-BL | 15 | -0.892 | 3.351 | 0.160 |
| | B | H-L | 15 | 0.008 | 2.303 | |

TABLE 3-continued

Summary of Results

| | | | | | |
|---|---|---|---|---|---|
| Superoxide Dismutase, mg SOD/mg Hb | A | L-BL | 15 | 0.007 | 0.036 | 0.233 |
| | A | H-L | 15 | -0.0260 | 0.063 | |
| | A | C-H | 15 | 0.041 | 0.120 | 0.104 |
| | B | L-BL | 15 | 0.001 | 0.055 | 0.4724 |
| | B | H-L | 15 | -0.051 | 0.065 | |
| Glutathione Peroxidase, mU GPx/mg Hb | A | L-BL | 15 | -0.378 | 2.922 | |
| | A | H-L | 15 | -0.411 | 1.174 | |
| | A | C-H | 15 | 0.216 | 1.068 | 0.223 |
| | B | L-BL | 15 | -0.170 | 0.949 | |
| | B | H-L | 15 | -0.770 | 1.274 | |
| Heme Oxygenase-1, ng/mL | A | L-BL | 15 | -0.209 | 0.403 | |
| | A | H-L | 15 | -0.004 | 0.3107 | |
| | A | C-H | 15 | 0.093 | 0.238 | 0.076 |
| | B | L-BL | 15 | 0.187 | 0.537 | 0.100 |
| | B | H-L | 15 | -0.074 | 0.244 | |
| Catalase, mg CAT/mg Hb | A | L-BL | 14 | -0.079 | 0.227 | 0.2958 |
| | A | H-L | 14 | -0.041 | 0.120 | 0.2412 |
| | A | C-H | 15 | -0.035 | 0.169 | 0.5416 |

The MDA as measured by colormetric and spectrometric methods did not correlate well and were not further considered.

Urine samples analyzed to obtain delta L-BL in participants from Group A indicated a statistically significant decrease in the levels of 8-isoprostane (−0.834 ng/mL, p=0.004) which is a favorable effect. Increasing the dose from the low dose (300 mg/day) to the high dose (600 mg/day) showed an increase in the 8-isoprostane (H-L=1.287), indicating an increase of oxidative stress in the system. Interestingly, the combination of the high dose of Blend A with the vitamins, minerals and color blend corrected the increased oxidative stress detected when the high dose of Blend A was taken alone. These favorable results (C-H=−0.830, p=0.077) also reached statistical significance.

Supplementation of Blend B at low dose showed a decrease of 8-isoprostane (L-BL=−0.892 ng/mL, p=0.077) in urinary 8-isoprostane, which is a favorable effect whereas the high dose had no effect on urinary 8-isoprostane (H-L=0.008, p=0.160).

With these examples, Blends A and B showed positive responses for SOD. For Blend A at low dose (L-BL=0.007) indicates a favorable increase in enzyme production. At the high dose of Blend A (H-L=−0.026), SOD decreased and therefore, did not respond in a favorable direction. The combination of high dose Blend A with vitamins, minerals and color blend increased SOD production, therefore, correcting the unfavorable trend in high dose alone (C-H=0.041, p=0.104). Supplementation with Blend B at the low dose also showed a favorable increase in SOD production (L-BL=0.001, p=0.472).

Blend A at the high dose in combination with the vitamin, mineral and color blend performed most favorably with respect to GSH-Px production. C-H delta is 0.216 with a p value of 0.223). For Blend A at low dose and high dose, there was a slight decrease in GSH-Px production.

Blend A at the high dose combined with the vitamin, mineral and color blend showed a favorable trend of inducing the production of HMOX-1 (C-H=0.093, p=0.0762). Blend A at low dose showed a slight decrease in HMOX-1 production, and when supplemented with high dose, there was no change in HMOX-1 production. Supplementation of Blend B at low dose also showed a favorable increase (L-BL=0.187, p=0.100) in this enzyme.

Subjects supplemented with Blend A were measured for their catalase activity. Blend A at low dose (L-BL) showed a more prominent decrease in catalase production, suggesting a strong effect compared to high dose (H-L) or combination dose (C-H).

All patents, patent applications, and literature references cited in this specification are hereby incorporated herein by reference in their entirety. In case of conflict, the present description, including definitions, will control.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A method for stimulating an antioxidant response element (ARE) and/or inducing Heme Oxygenase-1 (HOX-1) expression in the cells of a human in need thereof, comprising orally administering to said human an effective amount of a dietary supplement comprising turmeric, quercetin and rosemary, wherein the turmeric, quercetin and rosemary are present in the supplement in a ratio of 1:3:5, respectively.

2. The method of claim 1 wherein the orally administering step includes administering to the human the dietary supplement in the form of at least one of a capsule, tablet, and liquid form.

3. The method of claim 1 wherein turmeric in an amount of 33 mg, quercetin in an amount of 100 mg, and rosemary in an amount of 167 mg, are administered during the orally administering step.

4. The method of claim 1 wherein turmeric in an amount of 66 mg, quercetin in an amount of 200 mg, and rosemary in an amount of 333 mg, are administered during the orally administering step.

5. The method of claim 1 further comprising orally administering at least one of vitamins and minerals with the dietary supplement to the human.

6. The method of claim 1, wherein said orally administering to said human also decreases urinary level of 8-isoprostane and/or blood serum level of catalase in the human.

7. The method of claim 1, wherein said orally administering to said human also increases production of at least one of glutathione peroxidase and superoxide dismutase in the human.

8. The method of claim 1 wherein the turmeric is at least one of derived and extracted from *Curcuma longa*.

9. The method of claim 1 wherein the quercetin is at least one of derived and extracted from at least one of apples, onions, parsley, sage, tea, blueberries, blackberries, bilberries, Fava d'anta and *Sophora japonica*.

10. The method of claim 1 wherein the rosemary is at least one of derived and extracted from *Rosmarinus officinalis*.

* * * * *

UNITED STATES PATENT AND TRADEMARK OFFICE
CERTIFICATE OF CORRECTION

Page 1 of 1

PATENT NO. : 9,517,249 B2
APPLICATION NO. : 14/088765
DATED : December 13, 2016
INVENTOR(S) : David J. Fast et al.

It is certified that error appears in the above-identified patent and that said Letters Patent is hereby corrected as shown below:

In the Claims

Column 19, Claim 1, Line 20:
"(HOX-1)"
Should read:
-- (HMOX-1) --

Signed and Sealed this
Eighth Day of January, 2019

Andrei Iancu
*Director of the United States Patent and Trademark Office*

SEQUENCE LISTING

<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtgactcagc a                                                        11